(12) United States Patent
Gunura et al.

(10) Patent No.: US 10,271,660 B2
(45) Date of Patent: Apr. 30, 2019

(54) SEAT UNIT FOR WEARABLE SITTING POSTURE ASSISTING DEVICE

(71) Applicant: Noonee AG, Zurich (CH)

(72) Inventors: Keith Gunura, Zurich (CH); Olga Motovilova, Zurich (CH); Daniel Vafi, Zurich (CH)

(73) Assignee: Noonee AG, Zurich (CH)

( * ) Notice: Subject to any disclaimer, the term of this patent is extended or adjusted under 35 U.S.C. 154(b) by 0 days.

(21) Appl. No.: 15/769,426

(22) PCT Filed: Sep. 9, 2016

(86) PCT No.: PCT/EP2016/071361
§ 371 (c)(1),
(2) Date: Apr. 19, 2018

(87) PCT Pub. No.: WO2017/067706
PCT Pub. Date: Apr. 27, 2017

(65) Prior Publication Data
US 2018/0317662 A1   Nov. 8, 2018

(30) Foreign Application Priority Data

Oct. 21, 2015   (EP) .................................... 15190895

(51) Int. Cl.
*A47C 9/00* (2006.01)
*A47C 9/10* (2006.01)
(Continued)

(52) U.S. Cl.
CPC ............ *A47C 9/025* (2013.01); *A61F 5/0125* (2013.01); *A61H 3/008* (2013.01); *A61H 2201/165* (2013.01); *A61H 2201/1633* (2013.01)

(58) Field of Classification Search
CPC ....... A47C 9/025; A61F 5/0125; A61H 3/008; A61H 2201/165; A61H 2201/1633
(Continued)

(56) References Cited

U.S. PATENT DOCUMENTS 140,662 A * 7/1873 Wheat .................... A61F 5/0111
602/23
406,328 A * 7/1889 Yagn ....................... A63B 25/10
297/4 X
(Continued)

FOREIGN PATENT DOCUMENTS

EP       1 905 408 A1    4/2008
JP    2009-2791747 A    12/2009
(Continued)

OTHER PUBLICATIONS

Extended European Search Report dated May 10, 2016 issued in corresponding EP patent application No. 15190895.1.
(Continued)

*Primary Examiner* — Rodney B White
(74) *Attorney, Agent, or Firm* — Posz Law Group, PLC

(57) ABSTRACT

A seat unit for a wearable sitting posture assisting device includes at least one sitting means designed to form an adjustable and/or self-adjusting seat surface to be used in at least one at least partly sitting posture and in a walking mode, and a frame means designed to receive a weight force of a person sitting on the sitting means that is mounted on the frame means, and to a wearable sitting posture assisting device with such a seat unit.

20 Claims, 7 Drawing Sheets

Figure 1:
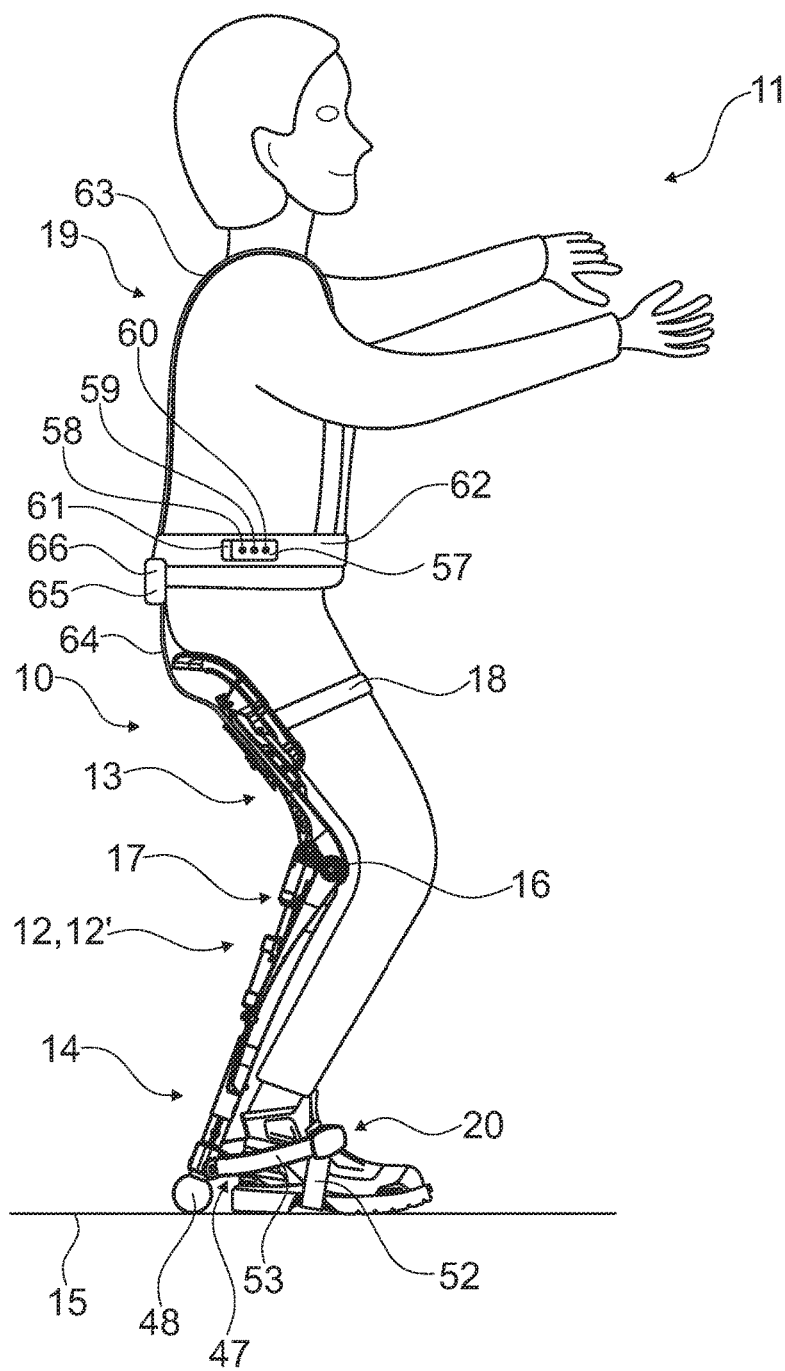

(51) Int. Cl.
  *A47C 1/00*  (2006.01)
  *A47C 9/02*  (2006.01)
  *A61F 5/01*  (2006.01)
  *A61H 3/00*  (2006.01)

(58) Field of Classification Search
  USPC .............................................. 297/4; 602/23
  See application file for complete search history.

(56) References Cited

U.S. PATENT DOCUMENTS

| | | | | |
|---|---|---|---|---|
| 671,638 A * | 4/1901 | Slagle | A47C 9/10 | 297/4 |
| 690,122 A * | 12/1901 | Slagle | A45B 5/00 | 297/4 X |
| 699,932 A * | 5/1902 | Smith | A47C 9/10 | 297/4 X |
| 2,099,345 A * | 11/1937 | Olszanowski | A47C 9/10 | 297/4 |
| 3,451,064 A * | 6/1969 | Dolan | A41D 1/06 | 297/4 X |
| 3,538,512 A * | 11/1970 | Dolan | A41D 1/06 | 297/4 X |
| 4,101,163 A * | 7/1978 | Morin | A47C 9/10 | 297/4 X |
| 4,138,156 A | 2/1979 | Bonner | | |
| 4,602,627 A * | 7/1986 | Vito | A61F 5/0102 | 602/23 |
| 4,641,882 A * | 2/1987 | Young | A47C 9/025 | 297/4 X |
| 4,930,839 A * | 6/1990 | Saito | A45B 5/00 | 297/4 X |
| 4,946,156 A * | 8/1990 | Hart | A61F 2/604 | 482/66 |
| 4,969,452 A * | 11/1990 | Petrofsky | A61F 5/0102 | 482/51 |
| 5,020,790 A * | 6/1991 | Beard | A61F 5/0102 | 482/4 |
| 5,178,595 A * | 1/1993 | MacGregor | A61H 3/02 | 135/68 |
| 5,230,700 A * | 7/1993 | Humbert | A61F 5/0104 | 135/65 |
| 5,476,441 A * | 12/1995 | Durfee | A61F 5/0102 | 434/112 |
| 5,927,797 A * | 7/1999 | Ferguson | A47C 7/022 | 297/4 |
| 5,961,476 A * | 10/1999 | Betto | A61F 5/0102 | 482/51 |
| 6,062,638 A * | 5/2000 | Ferguson | A47C 9/025 | 297/4 |
| 7,416,538 B2 * | 8/2008 | Katoh | A61F 5/0102 | 602/16 |
| 7,481,742 B2 * | 1/2009 | Katoh | A61F 5/0102 | 482/51 |
| 7,549,969 B2 * | 6/2009 | van den Bogert | A61F 5/0102 | 602/16 |
| 7,559,909 B2 * | 7/2009 | Katoh | A61F 5/0102 | 602/16 |
| 7,662,120 B2 * | 2/2010 | Hiki | A61H 3/008 | 602/16 |
| 7,731,673 B2 * | 6/2010 | Hiki | A61H 1/0237 | 602/16 |
| 7,798,983 B2 * | 9/2010 | Katoh | A61F 5/0102 | 601/5 |
| 7,854,715 B2 * | 12/2010 | Ashihara | A61F 5/0102 | 135/65 |
| 7,938,791 B2 * | 5/2011 | Shishido | A61H 3/008 | 601/5 |
| 7,947,004 B2 * | 5/2011 | Kazerooni | A61B 5/1038 | 602/16 |
| 7,963,932 B2 * | 6/2011 | Ashihara | A61F 5/0102 | 601/35 |
| 8,002,719 B2 * | 8/2011 | Ashihara | B25J 9/0006 | 601/33 |
| 8,083,695 B2 * | 12/2011 | Ashihara | A61F 5/01 | 601/33 |
| 8,114,034 B2 * | 2/2012 | Ikeuchi | A61H 3/00 | 601/5 |
| 8,142,371 B2 * | 3/2012 | Ikeuchi | A61H 3/008 | 601/23 |
| 8,202,234 B2 * | 6/2012 | Ikeuchi | A61H 3/008 | 601/23 |
| 8,303,524 B2 * | 11/2012 | Ikeuchi | A61H 3/008 | 482/66 |
| 8,388,558 B2 * | 3/2013 | Matsuoka | A61H 3/008 | 601/35 |
| 8,403,408 B2 * | 3/2013 | Hosler | A47C 9/025 | 297/4 |
| 8,523,790 B2 * | 9/2013 | Matsuoka | A61H 3/008 | 601/35 |
| 8,679,041 B2 * | 3/2014 | Noda | A61H 3/008 | 128/846 |
| 8,801,641 B2 * | 8/2014 | Kazerooni | A61H 3/008 | 128/898 |
| 8,968,222 B2 * | 3/2015 | Kazerooni | B25J 9/0006 | 224/265 |
| 8,968,223 B2 * | 3/2015 | Ikeuchi | A61H 3/008 | 601/23 |
| 2002/0082711 A1 * | 6/2002 | Kuhn | A61F 2/604 | 623/27 |
| 2002/0169402 A1 * | 11/2002 | Hatton | A61F 5/0125 | 602/26 |
| 2005/0242630 A1 * | 11/2005 | Miller | A01K 97/00 | 297/4 |
| 2006/0052731 A1 * | 3/2006 | Shimada | A61F 5/0102 | 602/5 |
| 2006/0052732 A1 * | 3/2006 | Shimada | A61F 5/0102 | 602/5 |
| 2006/0064047 A1 * | 3/2006 | Shimada | A61F 5/0102 | 602/23 |
| 2006/0130594 A1 * | 6/2006 | Ikeuchi | A61F 5/0102 | 73/862.08 |
| 2006/0155229 A1 * | 7/2006 | Ceriani | A61F 5/0125 | 602/16 |
| 2006/0155230 A1 * | 7/2006 | Mason | A61F 5/0125 | 602/16 |
| 2006/0155232 A1 * | 7/2006 | Ceriani | A61F 5/0125 | 602/23 |
| 2006/0167394 A1 * | 7/2006 | Ceriani | A61F 5/0123 | 602/16 |
| 2006/0178605 A1 * | 8/2006 | Sauber | A61F 5/0123 | 602/16 |
| 2006/0241539 A1 * | 10/2006 | Agrawal | B25J 9/0006 | 602/23 |
| 2006/0258967 A1 * | 11/2006 | Fujil | A61F 5/0102 | 602/23 |
| 2008/0009778 A1 * | 1/2008 | Hiki | A61F 5/0102 | 602/16 |
| 2008/0039756 A1 * | 2/2008 | Thorsteinsson | A61B 5/1038 | 602/23 |
| 2008/0125685 A1 * | 5/2008 | Bernardoni | A61F 5/0102 | 602/32 |
| 2008/0154165 A1 * | 6/2008 | Ashihara | A61F 5/0102 | 602/23 |
| 2008/0249438 A1 * | 10/2008 | Agrawal | A61H 1/0237 | 601/35 |
| 2009/0036815 A1 * | 2/2009 | Ido | A61H 1/0237 | 602/23 |
| 2009/0099494 A1 * | 4/2009 | Ashihara | A61H 3/008 | 602/23 |
| 2009/0259154 A1 * | 10/2009 | Nace | A61F 5/012 | 602/16 |
| 2009/0287125 A1 * | 11/2009 | Einarsson | A61F 5/0106 | 602/23 |
| 2009/0292232 A1 | 11/2009 | Ashihara et al. | | |
| 2009/0312844 A1 * | 12/2009 | Ikeuchi | A61H 3/008 | 623/40 |

(56) References Cited

U.S. PATENT DOCUMENTS

| | | | | |
|---|---|---|---|---|
| 2010/0004577 | A1* | 1/2010 | Yasuhara | A63B 23/04 602/23 |
| 2010/0036302 | A1* | 2/2010 | Shimada | A61F 5/0102 602/16 |
| 2010/0076360 | A1* | 3/2010 | Shimada | A61B 5/1038 602/23 |
| 2010/0094188 | A1* | 4/2010 | Goffer | A61H 3/008 602/23 |
| 2010/0227741 | A1* | 9/2010 | Rosenberg | A61F 5/0123 482/79 |
| 2011/0319801 | A1* | 12/2011 | Ital | A61F 5/0102 602/23 |
| 2012/0259259 | A1* | 10/2012 | Chugunov | A61F 5/0102 602/16 |
| 2013/0006159 | A1* | 1/2013 | Nakashima | A61H 1/024 602/23 |
| 2013/0324899 | A1* | 12/2013 | Lance | A61F 5/0125 602/26 |
| 2014/0221894 | A1* | 8/2014 | Nagasaka | A61H 3/00 602/23 |
| 2014/0276303 | A1* | 9/2014 | Matthews | A61F 5/0111 602/16 |
| 2015/0018739 | A1* | 1/2015 | Threlfall | A61H 3/02 602/23 |
| 2016/0135604 | A1* | 5/2016 | Kim | A47C 4/04 297/4 |
| 2016/0175180 | A1* | 6/2016 | Bond | A61H 3/00 602/23 |
| 2016/0199208 | A1* | 7/2016 | Fior | A61F 5/0102 602/23 |
| 2016/0331486 | A1* | 11/2016 | Nakatani | A61H 3/00 |

FOREIGN PATENT DOCUMENTS

| | | |
|---|---|---|
| JP | 2014-068866 A | 4/2014 |
| KR | 101344177 B1 | 12/2013 |

OTHER PUBLICATIONS

Office Action dated Mar. 20, 2018 issued in corresponding EP patent application No. 15190895.1.

International Search Report and Written Opinion of the International Searching Authority dated Nov. 7, 2016 for the corresponding international application No. PCT/EP2016/071361.

International Preliminary Report on Patentability of the International Searching Authority dated Oct. 2, 2017 for the corresponding international application No. PCT/EP2016/071361.

Office action dated Nov. 15, 2018 issued in corresponding KR patent application No. 10-2018-7014013 (and English translation thereof).

Office action dated Nov. 13, 2018 issued in corresponding JP patent application No. 2018-534085 (and English translation thereof).

* cited by examiner

SEAT UNIT FOR WEARABLE SITTING POSTURE ASSISTING DEVICE

CROSS REFERENCE TO RELATED APPLICATIONS

This application is a U.S. national stage application of PCT/EP2016/071361 filed on Sep. 9, 2016, which is based on European Patent Application No. 15190895.1 filed on Oct. 21, 2015, the contents of which are incorporated herein by reference.

STATE OF THE ART

The invention relates to a wearable sitting posture assisting device.

A posture assisting device is already known from document WO 2015/028373 A1.

The objective of the invention is, in particular, to increase a wearing comfort. The objective is achieved according to the invention by the features of patent claim 1, while advantageous embodiments and further developments of the invention may be gathered from the subclaims and the further independent claim.

ADVANTAGES OF THE INVENTION

By the invention a seat unit for a wearable sitting posture assisting device is proposed, comprising at least one sitting means designed to form an adjustable and/or self-adjusting seat surface to be used in at least one at least partly sitting posture and in a walking mode, and comprising a frame means designed to receive a weight force of a person sitting on the sitting means that is mounted on the frame means. Thus a seat unit is provided which can be adjusted to the physique of a person. Furthermore, the seat unit is self-adjusting to the posture of the person, particularly to the walking posture, the sitting posture or the partly sitting posture. Due to comprising a frame means, the sitting means can be designed in such a way that it is changeable. In summary, a seat unit can be provided which allows a personalization of its components, particularly at least of parts of the sitting means. A wearing comfort can be increased. "Provided" is herein to be understood, in particular, as specifically programmed, designed and/or equipped. A "sitting device" is herein, in particular, to be understood as a part or a group of parts, wherein at least one of the parts forms a seat surface designed to come into contact with the person sitting on the wearable sitting posture assisting device. A "wearable sitting posture assisting device" is herein to be understood as a device which is designed to receive a weight force of a person in a sitting posture or in a partly sitting and to transmit the weight force to a ground. In particular the wearable sitting posture assisting device is only designed to receive and transmit the weight force. The wearable sitting posture assisting device is not designed to generate a controllable force, which is provided to assist a person while walking, standing or lifting some loads. A "frame means" is herein to be understood, in particular, as a part or a group of part, which is provided to transmit the person's weight force, but which does not form the seat surface by itself. By an "adjustable and/or self-adjusting seat surface" is herein to be understood, in particular, that the seat surface or at least a portion of the seat surface is provided to be adjusted in relation to the frame means, either by the weight force of the person, resulting in a self-adjusting seat surface, or by a adjustable connection, resulting in an adjustable seat surface.

It is proposed that the seat unit comprises at least one rotatable connection between the sitting means and the frame means, which is designed to adjust an orientation at least of a portion of the sitting means with respect to the frame means. Thus, the sitting means can advantageously adjust and/or be advantageously adjusted to the respective leg and buttock of the person in different positions. A "rotatable connection" is herein to be understood, in particular, as a connection between at least one part of the sitting means and at least one part of the frame means, which provides an axis around which the at least one part of the sitting means is rotatable with respect to the at least one part of the frame means. Herein the at least one rotatable part of the sitting means preferably forms the seat surface or is at least rigidly connected to a part of the sitting means which forms the seat surface. The rotatable connection is preferably provided for self-adjusting of the seat surface.

It is further proposed that the seat unit comprises a displaceable connection between the sitting means and the frame means designed to adjust an axial position at least of a portion of the sitting means with respect to the frame means. Thus, the relative position of the seat unit can be adjusted to a length of the leg of the person. This allows adjusting the seat unit to the anatomy of the person. A "displaceable connection" is herein to be understood, in particular, as a connection between at least one part of the sitting means and at least one part of the frame means, which connection provides a distance by which the at least one part of the sitting means is movable with respect to the at least one part of the frame means. Herein the at least one displaceable part of the sitting means preferably forms the seat surface or is at least rigidly connected to a part of the sitting means which forms the seat surface. The displaceable connection is preferably provided for adjusting the seat surface.

It is further proposed that the sitting means comprises a sitting element, which forms the seat surface and which is designed to be arranged in at least two sitting positions, relative to the frame means. This makes sitting on the seat unit, which is usable in different sitting positions, particularly in the sitting posture or in a partly sitting posture, comfortable. "At least two sitting positions" are herein to be understood as two discrete sitting positions at which the sitting element can be adjusted as well as a continuous movability between the two sitting positions, to provide the self-adjusting of the seat surface.

It is further proposed that at least a portion of the seat surface has in at least one state a bent shape, which is provided for at least one of the sitting positions. Thus, the shape of the seat surface at least partly follows the anatomy of the upper leg and/or the buttocks of the person. Moreover, the seat unit allows comfortable usage when in a sitting or partly sitting position. Especially the bent shape can be used to create a sitting angle dependent force which acts on the sitting element and can be used to design the seat surface as self-adjusting. A "shape of the seat surface" is herein to be understood, in particular, as a form of the seat surface along a cross section which is orientated along a main extension direction of the sitting element.

It is further proposed that at least a portion of the seat surface has in at least one state an at least substantially flat shape, which is provided for at least one of the sitting positions. Thus, stable sitting on the seat unit is possible. Moreover, the person has the sensation of sitting on a flat surface. Especially a combination in which a portion of seat surface has a bent shape and a portion of the seat surface has a flat shape is useful to create a sitting angle dependent force which acts on the sitting element and can be used to design the seat surface as self-adjusting. In such an embodiment, the portion of the seat surface having the flat shape is preferably provided for the sitting posture, whereas the portion of the seat surface having the bent shape is preferably provided for the partly sitting posture.

It is further proposed that for the at least two different sitting positions, at least a portion of the sitting element is designed to be deflected by at least 10 degrees. Thus, the seat unit can be adjusted to different sitting positions, particularly dependent on the angle between the person's upper leg and lower leg when sitting or partly sitting. Moreover, the person has the sensation of sitting on a flat horizontal surface, similar to sitting on a conventional chair or stool. By "deflected" is herein to be understood, in particular, that a normalized orientation of at least a portion of the seat surface can be deflected by at least 10 degrees. The rotatable connection can be designed to provide a deflectability of at least a portion of the sitting element. In addition the sitting element can be made of an at least partially flexible material, preferably supported by a frame element. Particularly in such an embodiment the sitting element can be larger than the frame element, as a result of which the frame element supports the sitting element only in subareas. Thus the sitting element can be designed to provide a virtual chair edge. If the sitting element is at least partially made of an at least partially flexible material and forms a seat lip, the virtual edge for the sitting position is located close to the point farthest from the ground where the frame element supports the sitting element. If the person wearing the sitting posture assisting device is sitting on the sitting posture assisting device, the person will be under the impression that the better part of the weight force is transmitted through the part of the sitting element which is as far or farther away from the frame joint than the virtual edge of the sitting position. Furthermore, especially if at least a portion of the sitting element is flexible, the sitting element can be provided to feature a seat lip, especially in a partly sitting posture. Furthermore the sitting element can be designed as a non-slip surface, designed to provide a protrusion dependent on the sitting angle. Independently from this, the sitting element may feature a synthetic polymer or any suitable non-slip material to prevent slipping.

It is further proposed that the sitting element is designed to be deflected by the weight force of the person. Thus, the seat unit adjusts automatically to different sitting positions, particularly depending on the angle between the person's upper leg and lower leg when sitting or partly sitting. Moreover, the person has the sensation of sitting on flat horizontal surface automatically following the movement of the legs for different sitting positions, which results in the sensation of safe sitting in different postures.

It is further proposed that the seat unit comprises a restoring means, which is designed to move the sitting element into a basic position. Thus, easy handling of the seat unit is achieved. Moreover, no attention has to be paid to the proper positioning of the sitting element when moving from one position to another position. A "restoring means" is herein to be understood, in particular, as a means designed to move the sitting element back to a basic position. Preferably the restoring means is formed as a mechanical energy storage means, in particular by using a compressible element like a spring, especially a gas spring, or an element made of an elastic material. Alternatively the restoring means can also be formed as an actuator that is controlled by a control unit.

It is further proposed that in the walking mode the seat surface is designed to be orientated at least mainly perpendicular to the frame means. Thus, normal walking is possible while wearing the seat unit. Moreover, the seat surface is at least mainly parallel to the rear side of the thigh of the person when walking, resulting in a comfortable contact between the thigh and the seat surface. In this context, "orientated" is herein to be understood, in particular, as a normalized orientation of the surface, i.e. the orientation of a vector that is perpendicular to the surface.

It is further proposed that the basic position is provided for the walking mode. Thus, the sitting element automatically returns to a position where the seat surface is at least mainly parallel to the rear side of the thigh of the person. Moreover, normal walking is possible at any time when wearing the seat unit, particularly immediately after standing up from a sitting or partly sitting position.

It is further proposed that the sitting means provides a virtual chair edge for the at least partial sitting posture. Thus, the person has the sensation of sitting safely on the seat unit in all sitting postures, especially in the partly sitting posture. Moreover, the person has the sensation of sitting on a substantially horizontal surface with an edge, similar to sitting on a conventional chair or stool.

Furthermore a wearable sitting posture assisting device is proposed, having two leg units, each comprising an upper support designed to receive a weight force of a person, each having a seat unit according to the invention, a lower support designed to transmit the weight force to a ground, a joint pivotably connecting the upper support and the lower support to each other, and having a blocking means to block the joint. Such a wearable sitting posture assisting device can be adjusted to the anatomy of the person wearing the wearable sitting posture assisting device. Furthermore, a wearable sitting posture assisting device according to the invention is self-adjusting to the posture of the person, particularly to a walking posture, a sitting posture, or a partly sitting posture. Such a wearable sitting posture assisting device is modular, allowing personalization of its components. Moreover, outworn parts can be exchanged separately without the need of replacing the entire device. Herein a "main extension direction" of a part of the sitting posture assisting device is to be understood, insofar as not otherwise mentioned, in particular, a direction which is parallel to a plane that is perpendicular to an axis of the joint connecting the upper support and the lower support. In this context, "blocking" is to be understood, in particular, as at least an increasing of a damping rate of the a movement of the joint, in particular as a rigid connection of the joint.

It is proposed that the seat unit is designed to be deflected in dependence of a sitting angle between the upper support and the lower support. Thus, the seat unit can adjust to the posture of a person wearing the wearable sitting posture assisting device, particularly depending on the angle between the lower leg and the upper leg of the person, particularly when walking or sitting or partly sitting.

DRAWINGS

Further advantages may be gathered from the following description of the drawings. In the drawings one exemplary embodiment of the invention is depicted. The drawings, the description and the claims contain a plurality of features in combination. The person having ordinary skill in the art will purposefully also consider the features separately and will find further expedient combinations.

Figure 2:
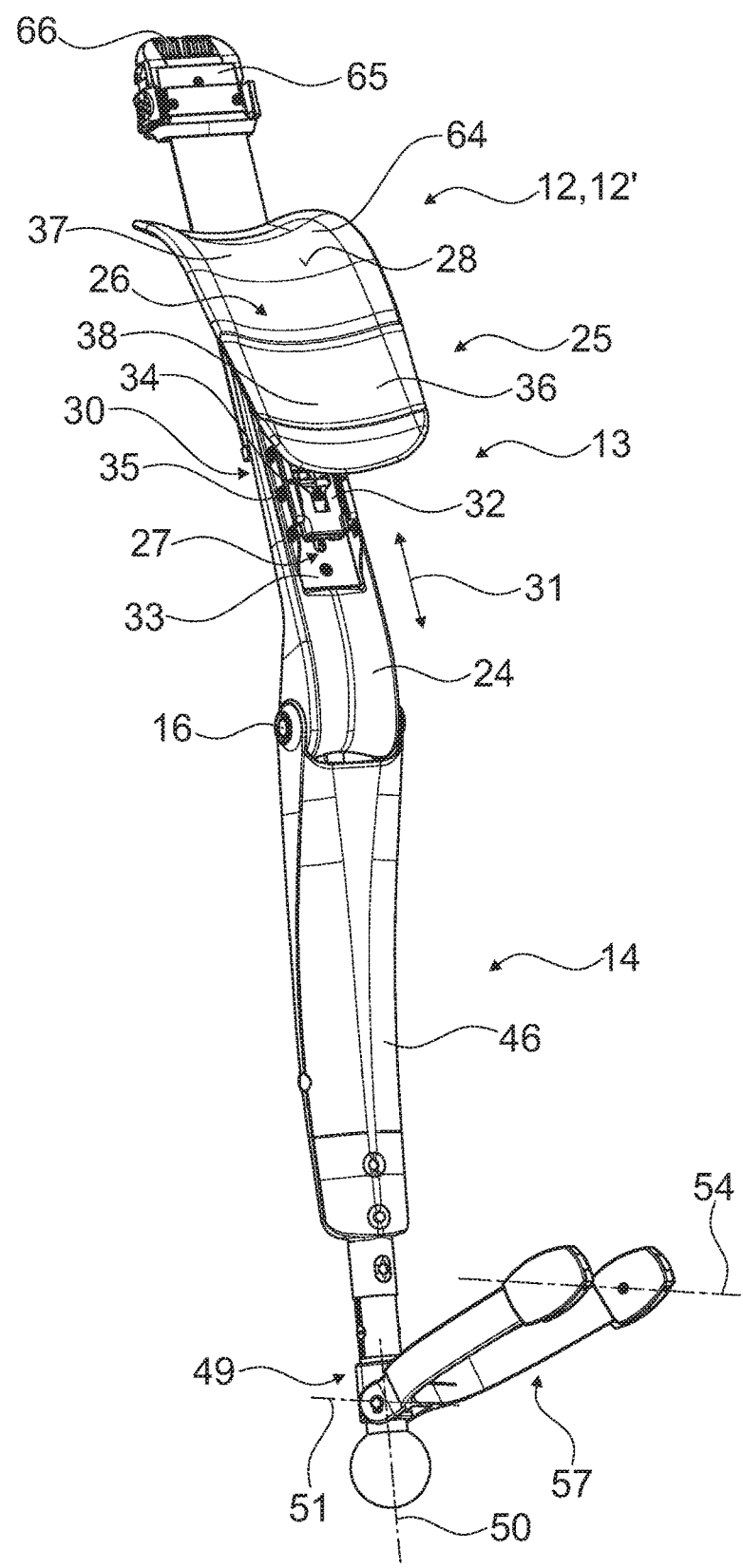
Figure 3:
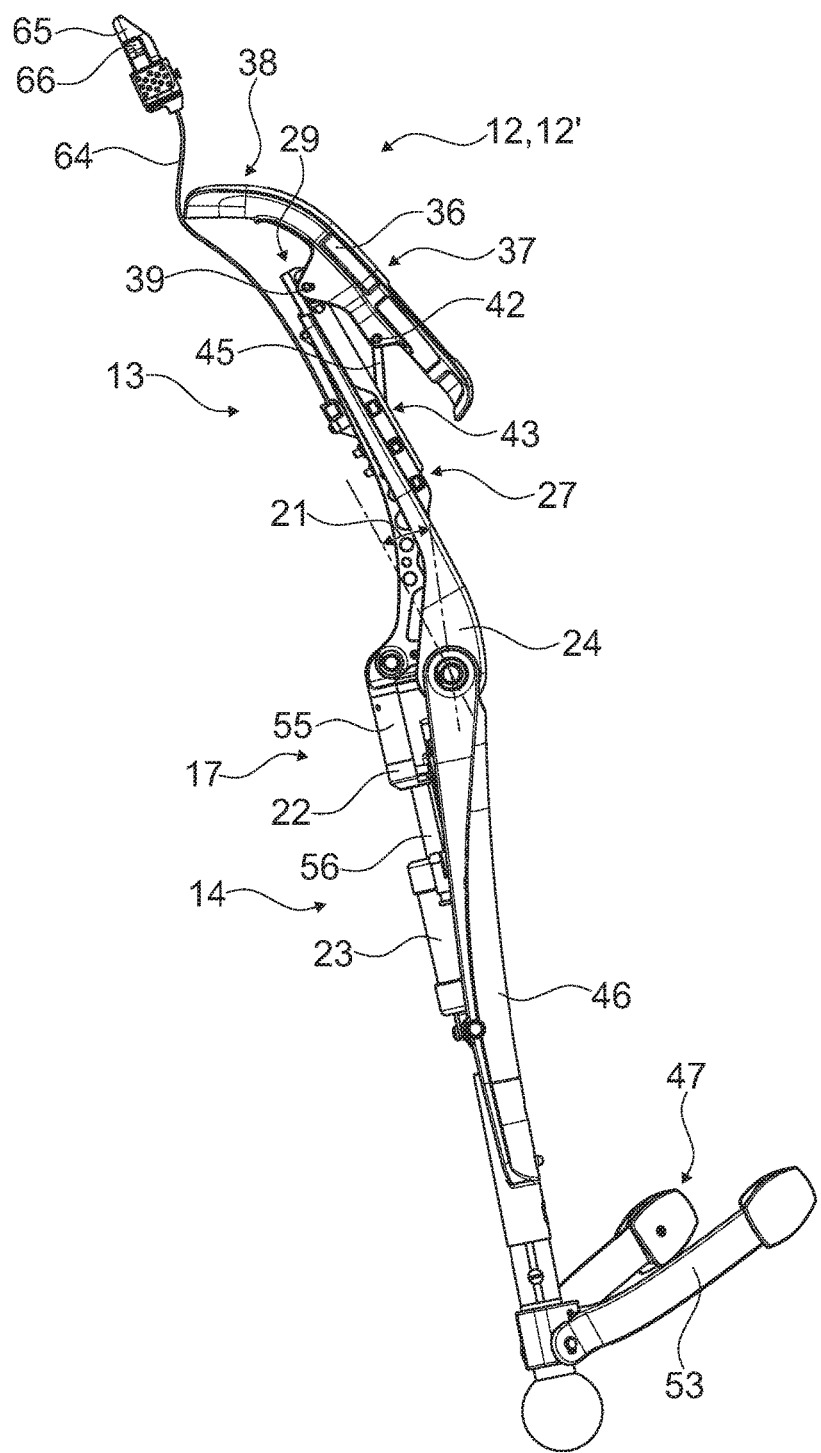
Figure 4:
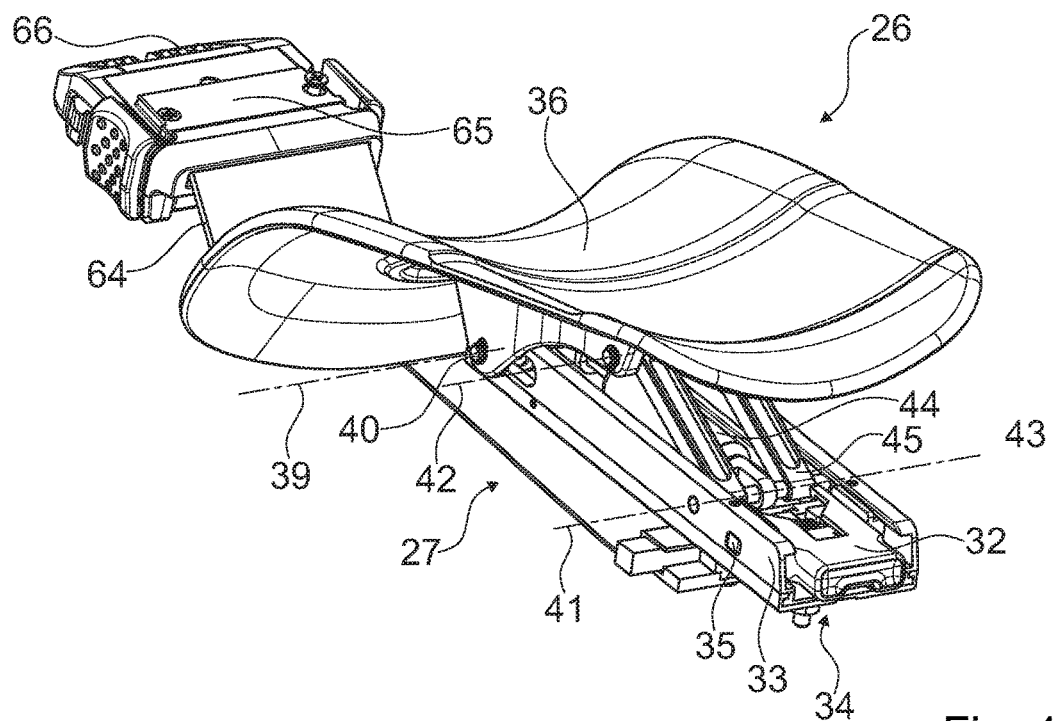
Figure 5:
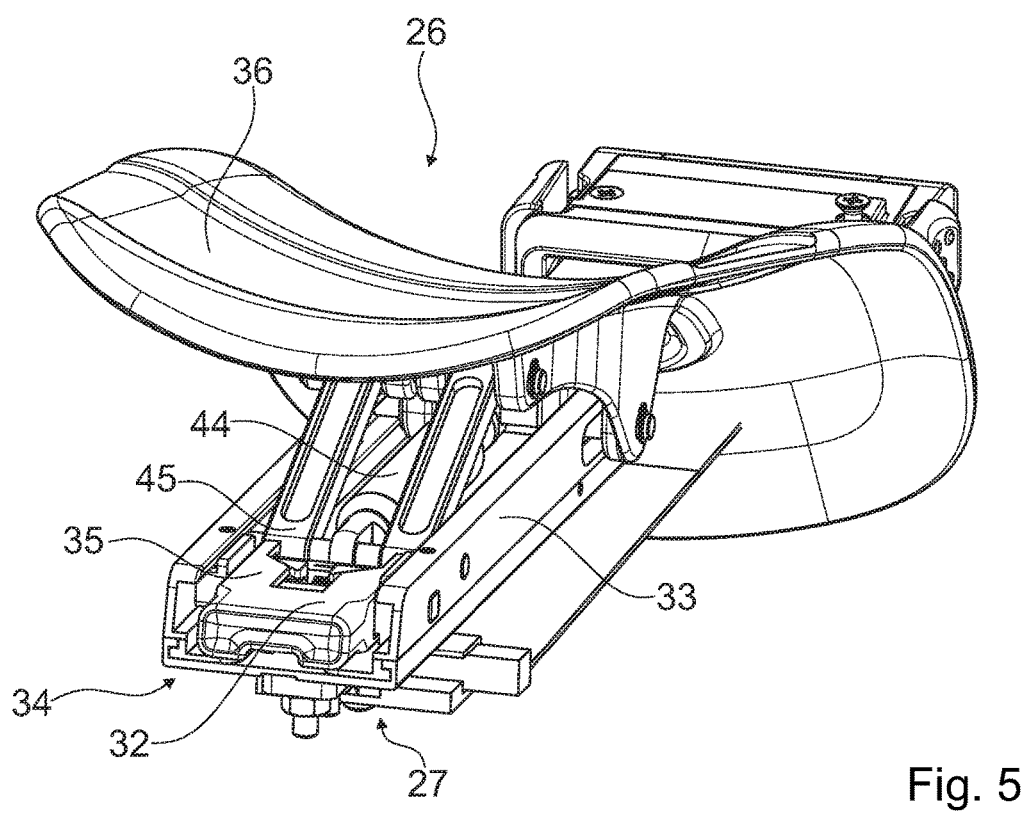
Figure 6:
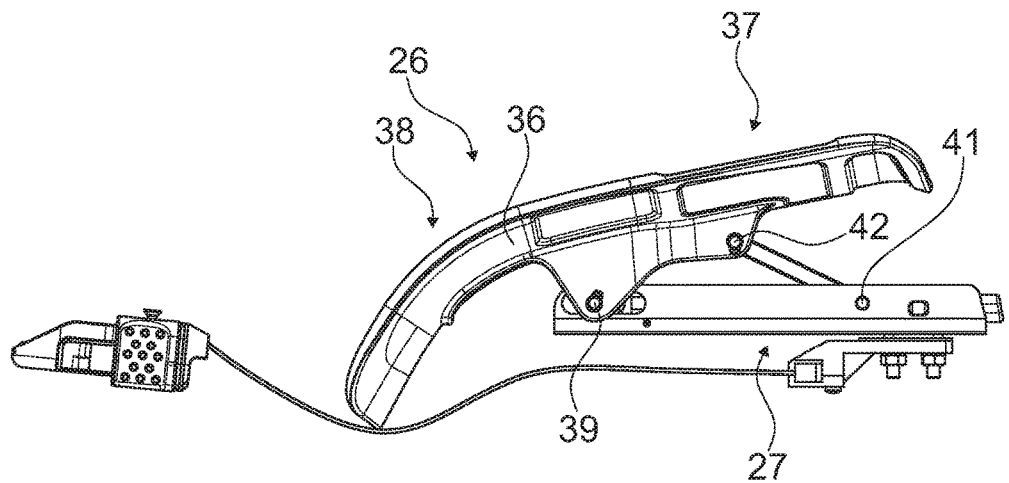
Figure 7:
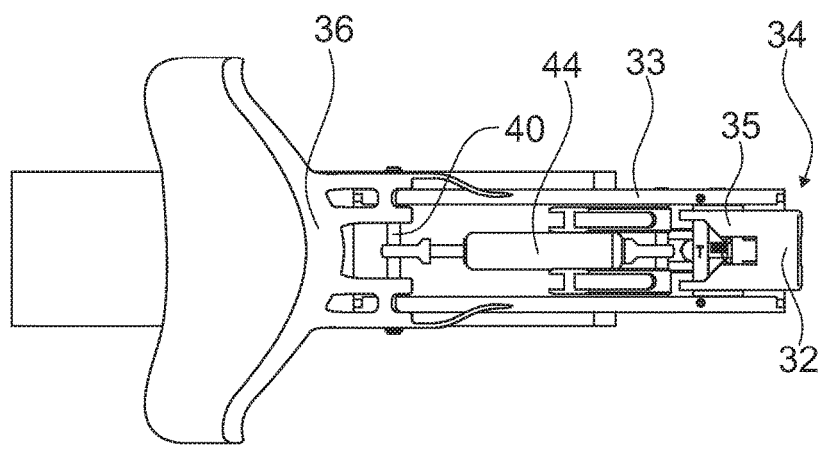
Figure 8:
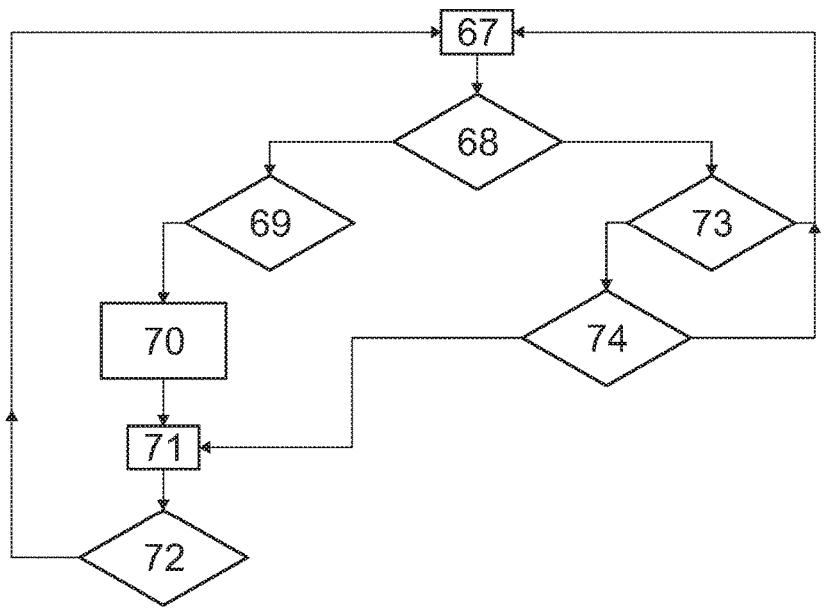
Figure 9:
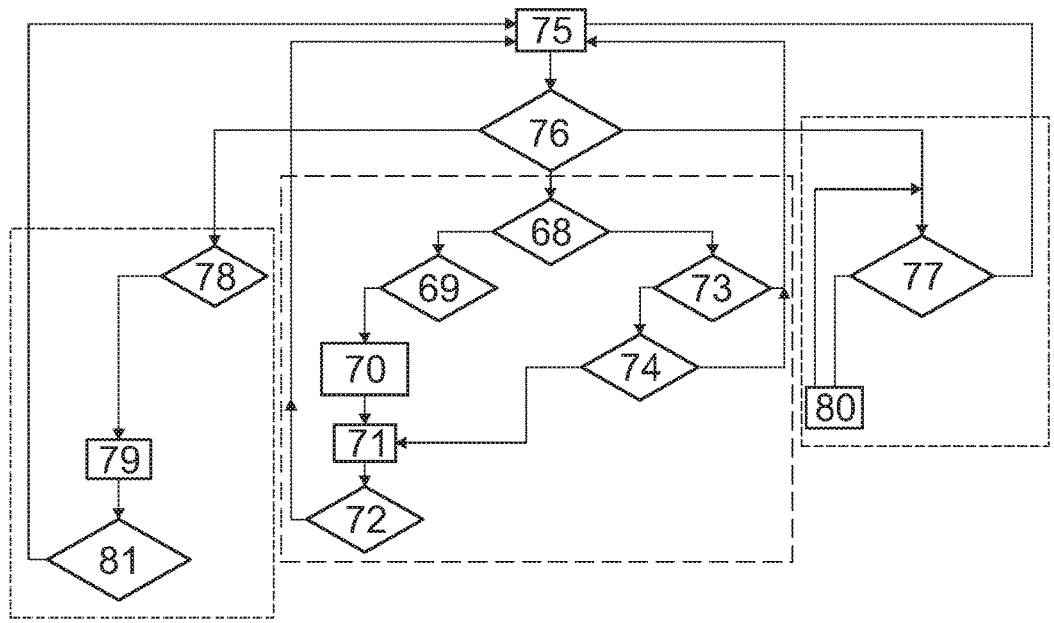
Figure 10:
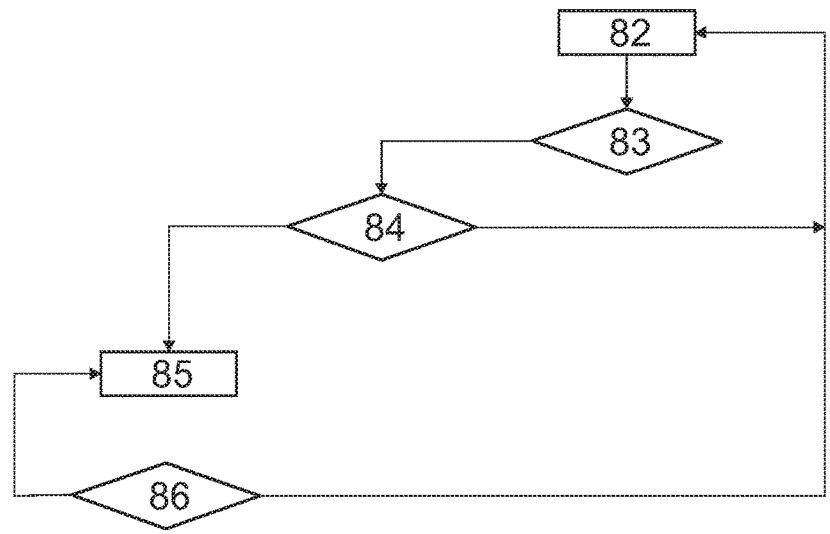
Figure 11:
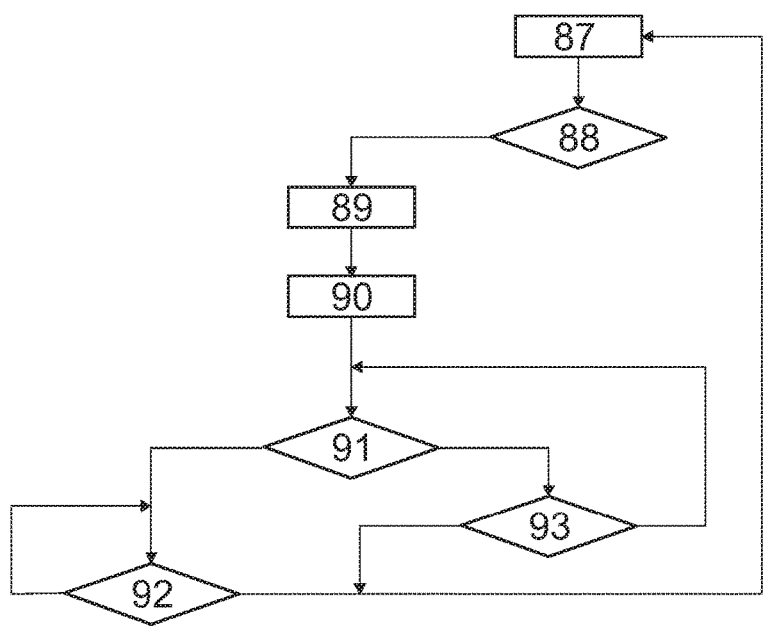

It is shown in:

FIG. 1 a person wearing a wearable sitting posture assisting device,

FIG. 2 a leg unit of the wearable sitting posture assisting device in a perspective view, FIG. 3 the leg unit of FIG. 1 in a side view, FIG. 4 a sitting means of the leg unit in a first perspective view, FIG. 5 the sitting means in a second perspective view, FIG. 6 a first cross section through the sitting means, FIG. 7 a second cross section through the sitting means, FIG. 8 a controlling scheme having two operations modes, provided to control blocking means of the leg units, FIG. 9 a controlling scheme having three operations modes, provided to control the blocking means of the leg units, FIG. 10 a controlling scheme using a sensor signal of a sitting sensor, FIG. 11 another controlling scheme using a sensor signal of a sitting sensor.

DESCRIPTION OF THE EXEMPLARY EMBODIMENT

FIG. 1 shows a wearable sitting posture assisting device 10, which is designed to assist a person 11 when taking a sitting or partly sitting posture. The sitting posture assisting device 10 is designed to be used in a sitting posture, in a partly sitting posture and in a walking mode. The wearable sitting posture assisting device 10 features a blocked state, in which the sitting posture assisting device 10 assists the person 11 wearing the sitting posture assisting device 10 when taking the sitting or partly sitting posture, and an unblocked state, in which the person 11 can walk while wearing the sitting posture assisting device 10. The wearable sitting posture assisting device 10 has two leg units 12, 12', each provided to be connected to a respective one of a person's legs. The leg units 12, 12' are designed equivalently. Because of this, merely one of the leg units 12, 12' is described in detail.

The leg unit 12 comprises an upper support 13 designed to receive a weight force of the person 11, a lower support 14 designed to transmit the weight force to a ground 15, a joint 16 pivotably connecting the upper support 13 and the lower support 14 to each other, and a blocking means 17 to block the joint 16 (cf. FIG. 2). The upper support 13 and the lower support 14 are designed to transmit the weight force if the joint 16 is blocked by the blocking means 17. In the blocked state the weight force of the person 11 is received by the upper support 13 and is transmitted to the lower support 14 by the joint 16 and the blocking means 17. In the blocked state, the upper support 13 and the lower support 14 form a seat on which the person 11 wearing the sitting posture assisting device 10 can sit.

The upper support 13 and the lower support 14 are each designed to be connected to the respective leg of the person 11 wearing the sitting posture assisting device 10. In the shown embodiment the upper support 13 comprises a thigh connection means 18 for connecting to a thigh of the person 11, and a body wearing unit 19 to be worn on a body of the person 11. The lower support 14 comprises a foot connection unit 20 for connecting the foot or a shoe of the person 11. In addition or alternatively, the lower support may comprise a lower leg connection means for connecting to the lower leg of the person. By connecting the lower support 14 to the shoe or to the lower leg and connecting the upper support 13 to the thigh, the sitting posture assisting device 10 follows a movement of the person's 10 leg in the walking mode. The lower support 14 is provided to be arranged to the rear of the person's 11 lower leg. The upper support 13 is provided to be arranged to the rear of the person's 11 thigh. The joint 16 is provided to be arranged to the rear of a person's 10 knee.

The joint 16 forms a knee joint, which is to be placed at least approximately at the same level as the person's 11 knee. While the person 11 is walking, the joint 16 follows at least approximately a movement of the person's 11 knee as an axis of the joint 16 is displaced in relation to an axis of the person's 11 knee. If the joint 16 is blocked by the blocking means 17, the upper support 13 and the lower support 14 are rigidly connected to each other. The blocking means 17 is designed to block the joint 16 at different sitting angles 21. The sitting angle 21 depends on whether the person 11 takes a sitting posture or a partly sitting posture. In the sitting posture the sitting angle 21 between the upper support 13 and the lower support 14 is at least 45 degrees. In the partly sitting posture the sitting angle 21 between the upper support 13 and the lower support 14 is less than 45 degrees. A fully stretched state of the joint 16 corresponds to a sitting angle 21 of 0 degrees. The lower the sitting posture is, the greater the sitting angle 21 becomes.

The blocking means 17 comprises a first blocking element 22 connected to the upper support 13 and a second blocking element 23 connected to the lower support 14 (cf. FIG. 3). The blocking means 17 is designed like a hydraulic damper, comprising a cylinder and a piston each functioning as one of the blocking elements 22, 23. In the unblocked state the two blocking elements 22, 23 are movable with respect to each other. In the blocked state the two blocking elements 22, 23 are rigidly connected to each other. The blocking means 17 is in particular constructed as a hydraulic blocking means. Other embodiments, e.g. a mechanic or an electromechanic blocking means, are also conceivable.

The upper support 13 comprises a base frame 24, which is connected to the lower support 14 by the joint 16. The base frame 24 forms a first joint element for the joint 16 connecting the upper support 13 and the lower support 14. The first blocking element 22 is connected to the base frame 24. The base frame 24 is provided to receive the person's 11 weight force. The weight force acting on the upper support 13 is fully received by the base frame 24. The weight force is then transmitted from the base frame 24 to the lower support 14 by the blocking means 17 and the joint 16.

The upper support 13 comprises a seat unit 25 (cf. FIG. 4). The seat unit 25 comprises a sitting means 26 and a frame means 27 movably mounted on the frame means 27. The sitting means 26 forms a seat surface 28. The seat surface 28 is designed to come into contact with the thigh of the person 11 sitting or partly sitting on the sitting posture assisting device 10. To adapt the sitting means 26 to a person's 11 anatomy, the seat surface 28 is adjustable. To increase a sitting comfort when taking a sitting posture or a partly sitting posture, the seat surface 28 is self-adjusting. The thigh connection means 18 comprises a thigh strap, which is designed to keep the seat surface 28 in contact with the thigh of the person 11 wearing the sitting posture assisting device 10.

The seat unit 28 is designed to be used in different postures, starting at a standing posture, which corresponds to the sitting angle 21 of 0 degrees, down to a sitting posture with a maximum sitting angle 21 of at least 80 degrees and preferably at least 90 degrees. By the way, the maximum sitting angle 21 can also be larger than 90 degrees. The seat unit 25 is designed to be worn in the walking mode as well as when taking a sitting or partly sitting posture. For the different sitting or partly sitting postures, the sitting means 26 of the seat unit 25 provides different sitting positions, in which the person 11 wearing the sitting posture assisting device 10 can sit or partly sit on the sitting means 26.

The frame means 27 of the seat unit 25 is designed to receive the weight force of the person 11 sitting or partly sitting on the sitting means 26. If the person sits or partly sits on the sitting posture assisting device 10, the weight force of the person 11 is transmitted through the sitting means 26 to the frame means 27 of the seat unit 25. From the frame means 27 of the seat unit 25 the weight force is transmitted to the base frame 24 of the upper support 13. Further on, the weight force is transmitted from the base frame 24 of the upper support 13 to the joint 16 and to the blocking means 17 connecting the upper support 13 and the lower support 14, and then transmitting to the lower support 14. Through the lower support 14 the weight force of the person 11 sitting on the sitting posture assisting 10 device is transmitted to the ground 15. In the shown embodiment, the lower support 14 is, at least in the sitting or partly sitting postures, in contact with the ground 15. As an alternative, it is also possible that the lower support 14 is designed to transmit the weight force of the person 11 via the person's 11 shoes. In the walking mode, in which the seat unit 25 can be used while the person 11 wearing the sitting posture assisting device 10 is walking or standing, the lower support 14 is at least partly lifted with respect to the ground 15.

To mount the sitting means 26 in such a way that it is movable on the frame means 27, the seat unit has at least one rotatable connection 29 between at least a portion of the sitting means 26 and the frame means 27 of the seat unit 25 (cf. FIG. 6). The rotatable connection 29 is designed for self-adjusting an orientation at least of a portion of the sitting means 26 with respect to the frame means 27. In the shown embodiment the rotatable connection 29 between the sitting means 26 and the frame means 27 is designed to allow an angle between the frame means 27 and the sitting means 26 to be changed by a rotation of the sitting means 26 with respect to the frame means 27. The angle is defined in a plane which has an orientation parallel to the axis of the joint 16 connecting the upper support 13 and the lower support 14. The rotatable connection 29 between the sitting means 26 and the frame means 27 allows aligning the sitting means 26 with the leg of the person 11 wearing the sitting posture assisting device 10. Whether the person 11 is sitting or partly sitting depends in particular on the sitting angle 21 enclosed by the upper support 13 and the lower support 14. If the person 11 is sitting or partly sitting, the weight force of the person 11 forces the sitting means 26 into a position which depends on the sitting angle 21 enclosed by the upper support 13 and the lower support 14.

Furthermore, the seat unit 25 has a displaceable connection 30 between the sitting means 26 and the frame means 27, which is designed to adjust an axial position of the sitting means 26 with respect to the frame means 27 (cf. FIG. 5). The displaceable connection 30 between the sitting means 26 and the frame means 27 allows adjusting the seat unit 25 to a length of the leg of the person 11 wearing the sitting posture assisting device 10. The displaceable connection 30 is providing a shiftability of the sitting means 26 along a main extension direction 31 of the frame means 27. The displaceable connection 30 between the sitting means 26 and the frame means 27 contains a carriage element 32, which is part of the sitting means 26, a rail element 33, which is part of the frame means 27, and a fixing means 34 which is provided to rigidly fix the carriage element 32 with respect to the rail element 33. The fixing means 34 is connected to the carriage element 32 and therefore a part of the sitting means 26, but may also be a part of the frame means 27. The fixings means 34 contains at least one pawl 35, which allows a latching of the carriage element 32 in at least two different positions with respect to the rail element 33. By fixing the displaceable connection 30, the sitting means 26 can, with respect to the displaceable connection 30, be rigidly connected to the frame means 27, after the position of the sitting means 26 has been adjusted with respect to the frame means 27. In the shown embodiment the displaceable connection 30 is designed to be fixed in three positions in a form-fit fashion. Alternatively the fixing means 34 can be designed to adjust the axial position of the sitting means 26 with respect to the frame means 27 continuously over a defined range and the sitting means 26 can be locked into any desired position within this range with respect to the frame means 27, especially if the displaceable connection 30 is provided to be fixed in a force-fit fashion. Advantageously the displaceable connection 30 between the sitting means 26 and the frame means 27 features at least one stopper element defining two stop points of maximum adjustability of the sitting means 26 at least substantially along the main extension direction 31.

The sitting means 26 comprises a sitting element 36, which forms the seat surface 28. Depending on a material the sitting element 36 consists of, the sitting means 26 may have a support structure partly supporting or tightening the sitting element 36. In the shown embodiment the sitting element 36 implements the support structure. As a result of this, the sitting element 36 and the support structure are embodied in a one-part-implementation. Additionally or alternatively the sitting means 26 may contain an additional frame element providing the support structure for supporting or tightening the sitting element 36. In particular, in such an embodiment the sitting element 36 is provided to be connected to the frame means 27 via the frame element of the sitting means 26.

The sitting element 36 is designed to be moved between a first sitting position, especially intended for the sitting posture, and a second sitting position, especially intended for the partly sitting posture, relative to the frame means 27. The sitting element 36, which forms the seat surface 28, is self-adjusting with respect to a rear side of the person's 11 thigh and/or buttock when the person 11 takes the sitting posture or partly sitting posture. The sitting element 36 is provided to be moved continuously between the first sitting position and the second sitting position. In the shown embodiment, the sitting element 36 is made of a stiff material, e.g. plastic, carbon composite material or a light metal, to form the seat surface 28 with a dimensionally stable shape. As mentioned before, the sitting element 36 can also be designed to have a flexible shape.

With respect to a cross section in the plane perpendicular to the axis of the joint 16, the sitting element 36 has a first portion 37 in which the seat surface 28 has a substantially flat shape, and a second portion 38, in which the seat surface 28 has a bent shape (cf. FIG. 6). The shape of the seat surface 28 is defined along the main extension direction 31 of the upper support 13. With reference to a transition between these two portions 37, 38, the portion 37 in which the seat surface 28 has the at least substantially flat shape extends towards the joint 16 connecting the upper support 13 and the lower support 14.

The portion 37 of the sitting element in which the seat surface 28 has the at least substantially flat shape is designed to come into contact with the rear side of the person's 11 thigh. This portion 37 is especially intended for the sitting posture. The portion 38 of the sitting element 36 in which the seat surface 28 has the bent shape is designed to come into contact with the person's 11 buttock. This portion 38 is especially intended for the partly sitting posture.

The frame means 27 has its main extension direction 31 which is orientated parallel to a direction along which the sitting means 26 is shiftable by the displaceable connection 30 with respect to the frame means 27. The rotatable connection 29 defines a main rotation axis 39 of the sitting means 26 around which the sitting element 36 is rotatable with respect to the frame means 27. To define the main rotation axis 39, the rotatable connection 29 comprises a bearing, in particular a roller bearing, preferably a plain bearing. The bearing is arranged in or nearby the transition between the portion 38 of the seat surface 28 having the bent shape and the portion 37 of the seat surface 28 having the at least substantially flat shape. The main rotation axis 39 of the sitting means 26 is fixed with respect to the seat surface's 28 shape. To define the main rotation axis 39, the rotatable connection 29 contains the bearing provided by the sitting element 36 and the carriage element 32 of the displaceable connection 30. The bearing contains a receptacle which is inserted in the sitting element 29, an axle 40 which is at least linearly fixed with respect to the sitting element 36, and a receptacle which is inserted in the carriage element 32. In an embodiment in which the sitting means 26 contains a frame element for the sitting element 36, the receptacle may also be inserted into the frame element instead of being inserted into the sitting element 36.

For the different sitting positions, the sitting element 36 is designed to be deflected by at least 5 degrees. In the shown embodiment, the sitting element 36 can be deflected by at least 30 degrees, while a higher deflectability may be also provided. The first sitting position which is designed for a sitting posture corresponds to an angle of the sitting element 36 of 0 degrees, the first sitting position is especially designed for sitting angles 21 above 50 degrees. The second sitting position which is designed for a partly sitting posture corresponds in particular to sitting angles 21 of less than 30 degrees.

The rotatable connection 29 provides a three-pivot-mount with two further axes 41, 42, which are parallel to the main rotation axis 39 of the first bearing. The rotational axes 41, 42 of the three-pivot-mount are at least substantially perpendicular to the main extension direction 31 of the frame means. The receptacle inserted in the carriage element 32 provides a guide structure, which is designed to guide the axle 40 of the bearing in a linear direction. The linear direction provided by the guide structure is orientated parallel to the main extension direction 31 of the frame means 27. By way of the guide structure, the main rotation axis 39 of the sitting element 36 is linearly movable. Due to its mounting the sitting element 36 can perform a sliding-rolling movement. The guide structure is formed as a guide channel inserted into the carriage element 32.

The sitting element 36 is designed to be deflected by the weight force of the person 11 sitting on the wearable sitting posture assisting device 10. The weight force of the person 11, especially in the partly sitting posture, acts as a torque rotating the sitting element 36 around the main rotation axis 39 of the sitting means 26. In the partly sitting posture the weight force acting on the portion 38 of the sitting surface having the bent shape is greater than the weight force acting on the portion 37 of the sitting portion having the flat shape. In the sitting posture the weight force acts the other way round. The torque provided by the person's 11 weight force forces the sitting element 36 into the different sitting positions. As the torque depends on the sitting angle 21, the sitting position taken by the sitting element 36 depends on the sitting angle 21. A deflection of the sitting element 36 is restricted by at least one stopping element. A range of the sitting angle 21 in which the sitting position of the sitting element 36 changes from the first sitting position to the second sitting position may vary. As the range can be very small, the person 11 sitting on the sitting posture assisting device 10 may have the impression that the sitting position of the sitting element 36 tilts at a certain sitting angle 21. In a preferred embodiment the range in which the sitting position changes is set between a sitting angle 21 of 40 degrees and a sitting angle 21 of 50 degrees.

The sitting means 26 comprises a restoring means 43, which is designed to move the sitting element 36 into a basic position (cf. FIG. 7). The basic position corresponds to the first sitting position, which is designed for the sitting posture. The restoring means 43 comprises a spring 44, which is provided to move the axle 40 of the bearing, which axle 40 defines the main rotation axis 39 of the sitting means 26. The axle 40 which bears the sitting element 36 is mounted on one end of the spring 44. During compression or decompression of the spring 44, the axle 40 connected to the spring 40 can move in the guide structure. The linear direction of the guide structure is at least substantially parallel to the main extension direction 31 of the frame means. The spring 44 is mounted between the axle 40 and the rail element 33. The spring 44 is preferably designed as a gas spring. Alternatively and/or additionally to the spring 44, a combination of a sensor and an actuator may be used to move the sitting element 36. Depending on the rotatable connection 29, the restoring means 43 may also be provided to directly generate a torque acting on the sitting element 36. For such an embodiment, the restoring means 43 may comprise a torsion spring.

To provide the three-pivot-mount, the rotatable connection 29 comprises a lever 45 providing the two further axes 41, 42. The lever 45 has a first end pivotably mounted to the carriage element 32 and a second end pivotably mounted to the sitting element 36. The lever 45 has a length which is smaller than a distance between the main rotation axis 39 and the axis 41 given by the first end of the lever 45. The lever 45 is provided to be rotated by an angle of at least 45 degrees. In the first sitting position of the sitting element 36, the lever 45 is orientated substantially parallel to the main extension direction 31 of the frame means 27. In the second sitting position, the lever 45 is rotated with respect to the first sitting position.

The sitting element 36 is designed to be arranged in the different sitting positions with respect to the frame means 27. If the person 11 wearing the sitting posture assisting device 10 is sitting or partly sitting on the sitting posture assisting device 10, the sitting element 36 is in close contact to the thigh and/or the buttock of the person 11. If the person 11 wearing the sitting posture assisting device 10 is sitting, the portion 37 of the seat surface 28 having the flat shape is substantially parallel to the thigh of the person 11. This is in particular the case if the sitting 21 angle between the upper support 13 and the lower support 14 is greater than 50 degrees and less than 90 degrees. In particular the thigh of the person 11 is then in contact with the portion 37 of the seat surface 28 formed by the sitting element 36, having the flat shape. If the sitting angle 21 is smaller, especially less than 40 degrees, the buttock of the person 11 comes into contact with the portion 38 of the seat surface 28 having the bent shape. As a result of this, the person's 11 weight force acts against the spring 44, the axle 40 is moved towards the lever 45, and the sitting element 36 becomes deflected. The spring 44 thus provides a very compact restoring means.

If the person 11 wearing the sitting posture assisting device 10 is walking, the sitting element 36 is at most in loose contact to the thigh and/or the buttock of the person 11. The restoring means 43 moves the sitting element 36 to the basic position which corresponds to the first sitting position. In the basic position the portion 37 of the seat surface 28 having the flat shape is orientated substantially parallel to the main extension direction 31 of the frame means 27. As the blocking means 17 is unblocked in the walking mode, the leg unit 12 follows the movement of the person's 11 leg while walking. The thigh connection means 18 and the foot connection unit 20 keep the leg unit 12 in contact with the person's 11 leg.

The lower support 14 comprises a base frame 46 and the foot connection unit 20 connected to the base frame 46 (cf. FIG. 2). The base frame 46 forms a second joint element for the joint 16 connecting the upper support 13 and the lower support 14. The second blocking element 23 of the blocking means 17 is connected to the base frame 46 of the lower support 14.

At least a portion of the foot connection unit 20 is rotatable relative to the base frame 46. The foot connection unit 20 comprises a shoe connector 47, which is rotatable with respect to the base frame 46. The foot connection unit 20 comprises a ground contact element 48, which is mounted on the base frame 46, and a rotatable connection 49, which arranges the shoe connector 47 in such a way that it is rotatable with respect to the base frame 46. The rotatable connection 49 has at least two axes 50, 51, which are perpendicular to each other. The first axis 50 is radially orientated with respect to the axis of the joint 16. The second axis 51 is parallelly orientated with respect to the axis of the joint 16.

The shoe connector 47, which is intended to fix the shoe of the person 11 wearing the sitting posture assisting device 10, comprises a shoe strapping element 52 and a mounting bracket 53, which are movably connected to each other (cf. FIG. 1). The strapping element 52 and the mounting bracket 53 in combination are intended to fix the person's 11 shoe. The shoe strapping element 52 is rotatable with respect to the mounting bracket 53 around an axis 54 which is parallel to the second axis 51 of the rotatable connection 49 of the foot connection unit 20. Due to at least a part of the foot connection unit 20 being rotatable relative to the base frame 46, the shoe connector 47 can follow the movement of the foot and/or shoe of the person 11 wearing the sitting posture assisting device 10. The ground contact element 48 is designed to come in contact with the ground 15 when the person is sitting or partly sitting. Thus, the weight force of the person is transmitted to the ground 15. As the upper support 13 is connected to the thigh of the person 11, the ground contact element 48 loses the contact to the ground 15 if the person 11 wearing the sitting posture assisting device 10 is standing or walking. Due to the rotatable connection 49 of the shoe connector 47, the lower support 13 is intended to be lifted with reference to the mounting bracket 53.

The shoe strapping element 52 can optionally be adjustably connected to the mounting bracket 53, by which the shoe strapping element 52 can be adjusted to the shoe of the person 11 wearing the sitting posture assisting device 10. The mounting bracket 53 may feature a clipping area, where the shoe strapping element 52 can be clipped to the mounting bracket 53 in at least two different positions. Thus, the shoe connector 47 can be adjusted to a length of the foot and/or shoe of the person 11 wearing the sitting posture assisting device 10.

The shoe strapping element 52 features a centre part, which at least partly comes into contact with the mounting bracket 53 when the shoe strapping element 52 is connected to the mounting bracket 53. The center part consists of a brace, which ends in one strap mount at each of its ends. The shoe strapping element 52 is connected to the mounting bracket 53 via the strap mounts. In this way the shoe strapping element 52 is rotatably connected to the mounting bracket 53. In another embodiment the mounting bracket 53 of the shoe connector 47 can be one-sided.

The entire shoe connector 47 is disconnectable from the ground contact element 48. A portion of the rotatable connection 49 between the shoe connector 47 and the ground contact element 48, providing the second axis 51, is designed as a quick-release fastener. When connecting the shoe connector 47 to the shoe of the person 11, the entire shoe connector 47 may be disconnected from the base frame 46 of the lower support 14. When the shoe strapping element 42 and/or the mounting bracket 53 has been adjusted to the shoe of the person 11 and the shoe connector 47 is connected with the person's 11 shoe, the shoe connector 47 can be connected to the ground contact element 48. In addition, the shoe connector 47 can be substituted if it is worn down.

In the shown embodiment, the ground contact element 48 comprises a ground contact surface which is designed to be placed on the ground 15, to transmit the person's 11 weight force to the ground 15. In another embodiment the rotatable connection 49 between the ground contact element 48 and the shoe connector 47 may be designed to transmit the person's 11 weight force. If the person 11 is sitting or partly sitting on the sitting posture assisting device 10, the weight force is transmitted to the shoe connector 47 via the ground contact element 48. The weight force is then transmitted from the shoe connector 47 to the ground 15 either directly or via the shoe of the person.

The leg unit 12 comprises an actuator 55, which is designed to control the blocking means 17. The blocking means 17 comprises a security mechanism, which allows the person 11 wearing the sitting posture assisting device 10 to stand up while the blocking means 17 is blocked. In the shown embodiment, the blocking means 17 comprises a valve designed to be closed by the actuator 55. The valve is designed like a back pressure valve, opening when the person stands up. The actuator 55 is designed as an electromotor, which is able to open and to close the valve.

The leg unit 12 comprises a sitting angle sensor 56, which is designed to provide a sensor signal representing the sitting angle 21 between the upper support 13 and the lower support 14. In the shown embodiment the sitting angle sensor 56 is designed as a linear sensor, which detects a distance between the two blocking elements 22, 23 of the blocking means 17. Alternatively, a rotation sensor or an angle sensor would also be sufficient. In the following, a sensor signal of 100 percent represents a fully stretched leg unit 12 and thereby a sitting angle 21 of 0 degrees, while a sensor signal of 0 percent represents a fully bent leg unit 12 and thereby a maximum sitting angle 21, which is preferably at least 90 degrees.

The wearable sitting posture assisting device 10 comprises a control unit 57, which is designed to control the two blocking means 17 of the two leg units 12, 12'. The control unit 57 is designed to control the two blockings means 17 in combination. The actuators 55 of the two leg units 12, 12' and the sitting angle sensors 56 of the two leg units 12,12 are connected to the control unit 57. Thereby, in controlling the blocking means 17 the control unit 57 is designed to differentiate between the sensor signals of the sitting angle sensors 56 of the two leg units 12, 12'. The control unit 57 is also designed to control each leg unit 12, 12' separately.

By controlling the leg units 12, 12' in combination or separately, the control unit 57 is designed to control the blocking means 17 in dependence of the sensor signal of the respective sitting angle sensor 56. On the one hand the control unit 57 is capable of detecting a movement of the respective leg unit 12, 12' by analyzing the sensor signal of the respective sitting angle sensor 56. On the other hand the control unit is capable of determining the actual sitting angle 21 of the respective leg unit 12, 12'. The control unit 57 has a blocking function which is designed to use both possibilities for controlling the blocking means 18.

To control one of the leg units 12, 12' separately or in combination, the blocking function is designed to differentiate between a movement and an idle state of the respective leg unit 12, 12' by analyzing the sensor signal. The blocking function is designed to block and to unblock the blocking means 17 of the respective leg unit 12, 12'. The control unit 57 has a manual blocking mode, in which the control unit 57 blocks or unblocks the blocking means 17 of the respective leg unit 12, 12' in dependence of an input signal of the person 11. If both leg units 12, 12' are connected to the control unit, the blocking means 17 of both leg units 12, 12' are blocked at the same time.

The control unit 57 comprises at least one input element 58, which is designed to be used by the person 11 wearing the sitting posture assisting device 10. The input element 58 is provided to create the input signal having states "yes" and "no". The input element 58 can be designed as a button which creates the input signal when pressed by the person 11. Other embodiments are also conceivable. In the shown embodiment, in which the at least one input element 58 is designed as a button, the state "yes" corresponds to a pressed state of the button whereas the state "no" corresponds to a released state of the button. In particular, the blocking function is provided to block or to unblock the blocking means 17 every time the person 11 presses the input 58 element. The control unit 57 changes a state of the blocking means 17, from the blocked state to the unblocked state and vice versa, by using the blocking function.

If the blocking means 17 of the respective leg unit 12, 12' is blocked and the control unit 57 detects a movement of one of the leg units 12, 12', the control unit 57 is provided to unblock the blocking means 17. This is in particular the case if the person 11 is in the sitting or partly sitting posture and then stands up making use of the security mechanism which allows standing up while the blocking means 17 is blocked. The blocking function, which is designed to differentiate between the movement and the idle state of the respective leg unit 12, 12' by analyzing the sensor signal, can also be used to block the blocking means 17 automatically, e.g. by determining a period for which the sensor signal remains constant.

To control the leg units 12, 12' in combination, the control unit comprises a comparison function which is designed to compare the sitting angles 21 of the two leg units 12, 12'. The comparison function is in particular designed to determine whether the sitting angles 21 of the two leg units 12, 12' are equal within a defined range. Two sitting angles 21 are defined to be equal if they differ by no more than 5 degrees. The comparison function may be used to block the blocking means 17 of the two leg units 12, 12' automatically. The operation program of the control unit may have a blocking mode designed to block the two leg units 12, 12' at the same sitting angle 21. If the two sitting angles 21 are equal for a defined period, the blocking means 17 are blocked. In the blocking mode the operation program is designed to compare the two sitting angles 21 by the comparison function.

The control unit 57 has a memory function, which is designed to save a sitting angle 21 and to restore the saved sitting angle 21. The memory function is designed to save an actual sitting angle 21. The control unit comprises an input element 59, which is designed to provide an input signal provided to call up the memory function. If the person presses the input element 59, the control unit 57 saves the actual sitting angle 21, preferably independently of whether the blocking means is blocked or unblocked, or restores the saved sitting angle 21.

The operation program has a memory mode designed to block the leg units 12, 12' at the sitting angle 21 saved by the blocking function and the memory function. To activate the memory mode, the control unit comprises a further input element 60. The control unit 57 is designed to switch between the blocking mode, which may in particular be split up between the blocking mode for manual blocking and the blocking mode for automatic blocking, and the memory mode, every time the input element 60 is pressed. In the shown embodiment, the control unit 57 comprises the three input elements 58, 59, 60. A number of the input elements 58, 59, 60 may be reduced if one or more of the input elements 58, 59, 60 are used twice.

The operation program is designed to compare the sitting angles 21 of the two leg units 12, 12 for blocking and unblocking the leg units 12, 12'. For example, the leg units 12, 12' are only blocked if the sitting angles 21 of the two leg units 12, 12' are equal to the saved sitting angle 21 within the given range for comparison of the sitting angles 21 being equal. If the person sits down, both leg units 12, 12' are bent at equal sitting angles 21. As soon as the sitting angles 21 reach the saved sitting angle 21, the control unit 57 blocks the blockings means 17 and the person has taken the sitting or partly sitting posture, which corresponds to the saved sitting angle 21. If the person stands up, the control unit unblocks the blockings means. By using the memory mode a person can stand up and sit down multiple times without using one of the input elements.

The control unit is attached to the body wearing unit 19. The body wearing unit 19 comprises a mount 61, in which the control unit 57 is mounted, the mount 61 providing an electrical connection towards the leg units 12, 12. Each of the leg units 12, 12' comprises a connector designed to connect the actuator 55 and the sitting angle sensor 56 of the respective leg unit 12, 12' to the control unit 57. As the leg units 12, 12' are equivalent, a sequence and an arrangement of connecting the leg units 12, 12' to the control unit 57 is insignificant. Each of the leg units 12, 12' can be worn on the left leg or on the right leg. In this way, the two leg units 12, 12' are equivalent and the control unit is separated from the leg units 12, 12', the wearable sitting posture assisting device 10 is designed in a modular manner. The control unit 57, the body wearing unit 19 and each of the leg units 12, 12' can be replaced separately.

The wearable sitting posture assisting device comprises the body wearing unit 19, which is in particular provided to increase a wearing comfort. The body wearing unit comprises at least a waist belt unit 62. In the shown embodiment, the body wearing unit 19 comprises in addition a shoulder belt unit 63. The leg units 12, 12' are attached to the waist belt unit 62. Each of the leg units 12, 12' comprises a strap 64 providing a mechanical connection of the upper support 13 with the waist belt unit 62, and comprises a strap connector 65 enabling the mechanical connection to be detachable. In addition, each of the leg units 12, 12' comprises an electrical connector 66 providing a detachable electrical connection of the actuator 55 and the sitting angle sensor 56 with the control unit 58. The strap connection 65 and the electrical connector 66 are embodied in a one-part implementation. In this way, the mechanical connection and the electrical connection are provided to be attached and detached together.

In the following, four implementations of the operation program will be exemplarily described in more detail. The implementations are using the above-described modes and functions at least partially. The implementations have different function blocks which can be combined in different manner. In the following description, a "decision step" is to be understood, in particular, as a step in which a signal is analyzed for fulfilling at least one condition or not. Insofar as a decision step has only one subsequent processing path, the decision step may be understood as an event step, e.g. the decision step is held until the condition is fulfilled. A "process step" is to be understood, in particular, as a step in which a process is performed, for example blocking or unblocking the leg units.

The first implementation features the memory mode (cf. FIG. 8). The first implementation depends on the input signal of the person 11, which is provided by the input element 58 and has the states "yes" and "no". In a first process step 67 all leg units 12, 12' are unblocked. If in a first decision step 68 the input signal provided by the input element 58 has the state "yes", which in particular corresponds to a pressed button, nothing happens until in a further decision step 69 the input signal has the state "no", which corresponds in particular to a released button. Afterwards, in a process step 70, the actual sitting angle 21 has been saved as a reference sitting angle 21. In a subsequent process step 71, the leg units 12, 12' are blocked. If in a decision step 72 the sitting angle 21 exceeds a predefined range with respect to the stored sitting angle 21, the operation program returns to the first process step 67, in which the leg units 12, 12' are unblocked. If in the decision step 68 the input signal is "no", it is checked in a subsequent decision step 73 whether a sitting angle 21 has been saved. If a sitting angle 21 has been saved, in a subsequent decision step 74 the actual sitting angle 21 is checked for being within the predefined range for the saved sitting angle 21. Otherwise the operation program goes to the initial process step 67. If it is verified in the decision step 74 that the sitting angle 21 is within the predefined range, the operation program goes to the process step 71, in which the leg units 12, 12' are blocked. Otherwise the operation program returns to the initial process step 67.

The second implementation features the manual blocking mode, the automatic blocking mode and the memory mode, which are selectable by the person 11 (cf. FIG. 9). The second implementation depends on the input signal provided by the input element 59, which is designed to switch between the manual blocking mode, the automatic blocking mode and the memory mode. While the leg units 12, 12' are unblocked, the manual blocking mode, the automatic blocking mode or the memory mode is selected in a first decision step 76. To unblock the leg units 12, 12' this implementation has a process step 75. The memory mode is implemented as described for the first implementation, wherein the process step 75 substitutes the process step 67.

For the automatic blocking mode, the implementation has a first decision step 77, in which a movement of the leg units 12, 12' is checked. If the sitting angle 21 is constant within a predefined tolerance interval over a predefined time period, the leg units 12, 12' are blocked in a process step 80. Otherwise the operation program returns to the process step 75 and the leg units 12, 12' are kept unblocked or will be unblocked.

For the manual blocking mode the implementation contains a first decision step 78, in which an input signal is checked. If the input signal has the state "yes", which in particular corresponds to a pressed and/or released button, all leg units 12, 12' are blocked in a subsequent process step 79. In a subsequent decision step 81 is checked whether the sitting angle 21 exceeds a range around the sitting angle 21, the leg units 12, 12' are blocked in. If the sitting angle 21 exceeds the range, the operation program returns to the initial process step 75.

The third implementation and the fourth implementation are provided for a wearable sitting posture assisting device having at least one sitting sensor (cf. FIG. 10). In a preferred embodiment of such a wearable sitting posture assisting device, each of the leg units 12, 12' comprises a sitting sensor, which is designed to detect the sitting or partial sitting posture. The sitting sensor may be embodied as a load-balanced sensor provided to determine the transmitted weight force or may be embodied as a ground contact sensor provided to capture a ground contact of the ground contact element 48. Other embodiments are also conceivable.

The third implementation features the manual blocking mode supplemented by an analysis of a sensor signal provided by the sitting sensor. The third implementation depends on the input signal provided by the input element 58, having the states "yes" or "no", and on the sensor signal of a sitting sensor, having a state "yes" corresponding to a sitting or partial sitting posture, and a state "no" corresponding to the standing posture or the walking mode. In an initial process step 82, all leg units 12, 12' are unblocked. In a subsequent decision step 83, the input signal provided by the input element 58 is checked for having the state "yes". If in the decision step 83 the input signal has the state "yes", in a further decision step 84 the sensor signal of the sitting sensor is checked also for having the state "yes", which corresponds to the sitting or partly sitting posture. If the sensor signal has the state "yes" in a following process step 85 all leg units 12, 12' are blocked. If the sensor signal has the state "no" in the decision step 84 or in a decision step 86 following the process step 85, the operation program returns to the initial process step 82. In the third implementation the control unit 58 will block the leg units 12, 12' only if the sitting sensor is active, after a corresponding input signal of the person 11. If the person 11 stands up, the leg units 12, 12' are immediately unblocked.

The fourth implementation features the manual blocking mode supplemented by an analysis of a sensor signal provided by the sitting sensor, and by a security timer preventing an untimed unblocking of the leg units 12, 12' (cf. FIG. 11). The fourth implementation depends on the input signal provided by the input element 58, having the states "yes" or "no", and on the sensor signal of a sitting sensor, having a state "yes" corresponding to a sitting or partial sitting posture, and a state "no" corresponding to the standing posture or the walking mode. In an initial process step 87, the leg units 12, 12' are unblocked. If the input signal is "yes" in a subsequent decision step 88, in a process step 89 the security timer is started. In a further subsequent process step 90, the leg units 12, 12' are blocked. In a subsequent decision step 91 is checked whether the sensor signal of the sitting sensor has the state "yes" or the state "no". If the sensor signal has the state "yes", the leg units 12, 12' are kept blocked until the sensor signal has the state "no", which corresponds to standing up and which is checked in a further decision step 92. In this case, the operation program returns to the initial process step 87. If the sensor signal is "no" in the decision step 91, in a decision step 93 is checked whether the security timer exceeds a predefined time limit. If the time limit is not exceeded, the operation program returns to the decision step 91. Otherwise the operation program returns to the initial process step 87. The time limit is a predefined period which is required to allow the person 11 to activate the sitting sensor after taking the sitting or partly sitting posture. As a security feature the operation program blocks the leg units 12, 12' only for the time period before the leg units 12, 12' are unblocked, for example if the person 11 blocks the leg units 12, 12' untimely. When the person 11 actuates the corresponding input element 58, the control unit 58 always blocks the leg units 12, 12'. For the period when the sitting sensor has the state "yes", which corresponds to the sitting or partly sitting posture, the leg units 12, 12' remain blocked. If the person 11 stands up, the leg units 12, 12' are unblocked immediately.

The invention claimed is:

1. A wearable sitting posture assisting device, having two leg units, each leg unit comprising
    an upper support designed to receive a weight force of a person,
    a seat unit,
    a lower support designed to transmit the weight force to a ground,
    a joint pivotably connecting the upper support and the lower support to each other, and
    a blocking means to block the joint, wherein
    the seat unit comprises at least one sitting means designed to form an adjustable and/or self-adjusting seat surface to be used in at least one at least partly sitting posture and in a walking mode,
    the seat unit comprises a frame means designed to receive a weight force of a person sitting on the sitting means that is mounted on the frame means,
    the seat unit comprises at least one rotatable connection between the sitting means and the frame means designed to adjust an orientation at least of a portion of the sitting means with respect to the frame means, and
    the seat unit is designed to be deflected in dependence on a sitting angle between the upper support and the lower support.

2. The wearable sitting posture assisting device according to claim 1, wherein the seat unit comprises a displaceable connection between the sitting means and the frame means designed to adjust an axial position at least of a portion of the sitting means with respect to the frame means.

3. The wearable sitting posture assisting device according to claim 1, wherein at least a portion of the seat surface has in at least one state a bent shape, which is provided for at least one of the sitting positions.

4. The wearable sitting posture assisting device according to claim 1, wherein at least a portion of the seat surface has in at least one state an at least substantially flat shape, which is provided for at least one of the sitting positions.

5. The wearable sitting posture assisting device according to claim 1, wherein in the walking mode the seat surface is designed to be orientated at least mainly perpendicular to the frame means.

6. A wearable sitting posture assisting device, having two leg units, each leg unit comprising
    an upper support designed to receive a weight force of a person,
    a seat unit,
    a lower support designed to transmit the weight force to a ground,
    a joint pivotably connecting the upper support and the lower support to each other, and
    a blocking means to block the joint, wherein
    the seat unit comprises at least one sitting means designed to form an adjustable and/or self-adjusting seat surface to be used in at least one at least partly sitting posture and in a walking mode,
    the seat unit comprises a frame means designed to receive a weight force of a person sitting on the sitting means that is mounted on the frame means,
    the seat unit comprises at least one rotatable connection between the sitting means and the frame means designed to adjust an orientation at least of a portion of the sitting means with respect to the frame means,
    the sitting means comprises a sitting element, which forms the seat surface and which is designed to be arranged in at least two sitting positions, relative to the frame means, and
    at least a portion of the sitting element is designed to be deflected by the weight force of the person.

7. The wearable sitting posture assisting device according to claim 6, wherein the seat unit comprises a displaceable connection between the sitting means and the frame means designed to adjust an axial position at least of a portion of the sitting means with respect to the frame means.

8. The wearable sitting posture assisting device according to claim 6, wherein at least a portion of the seat surface has in at least one state a bent shape, which is provided for at least one of the sitting positions.

9. The wearable sitting posture assisting device according to claim 6, wherein at least a portion of the seat surface has in at least one state an at least substantially flat shape, which is provided for at least one of the sitting positions.

10. The wearable sitting posture assisting device according to claim 6, wherein for the at least two different sitting positions, the sitting element is designed to be deflected by at least 10 degrees.

11. The wearable sitting posture assisting device according to claim 6, wherein in the walking mode the seat surface is designed to be orientated at least mainly perpendicular to the frame means.

12. The wearable sitting posture assisting device according to claim 6, wherein the sitting means provides a virtual chair edge for the at least partly sitting posture.

13. A wearable sitting posture assisting device, having two leg units, each leg unit comprising
    an upper support designed to receive a weight force of a person,
    a seat unit,
    a lower support designed to transmit the weight force to a ground,
    a joint pivotably connecting the upper support and the lower support to each other, and
    a blocking means to block the joint, wherein
    the seat unit comprises at least one sitting means designed to form an adjustable and/or self-adjusting seat surface to be used in at least one at least partly sitting posture and in a walking mode,
    the seat unit comprises a frame means designed to receive a weight force of a person sitting on the sitting means that is mounted on the frame means,
    the seat unit comprises at least one rotatable connection between the sitting means and the frame means designed to adjust an orientation at least of a portion of the sitting means with respect to the frame means, the sitting means comprises a sitting element, which forms the seat surface and which is designed to be arranged in at least two sitting positions, relative to the frame means, and the seat unit comprises a restoring means, which is designed to move the sitting element into a basic position.

14. The wearable sitting posture assisting device according to claim 13, wherein the seat unit comprises a displaceable connection between the sitting means and the frame means designed to adjust an axial position at least of a portion of the sitting means with respect to the frame means.

15. The wearable sitting posture assisting device according to claim 13, wherein at least a portion of the seat surface has in at least one state a bent shape, which is provided for at least one of the sitting positions.

16. The wearable sitting posture assisting device according to claim 13, wherein at least a portion of the seat surface has in at least one state an at least substantially flat shape, which is provided for at least one of the sitting positions.

17. The wearable sitting posture assisting device according to claim 13, wherein for the at least two different sitting positions, the sitting element is designed to be deflected by at least 10 degrees.

18. The wearable sitting posture assisting device according to claim 13, wherein in the walking mode the seat surface is designed to be orientated at least mainly perpendicular to the frame means.

19. The wearable sitting posture assisting device according to claim 13, wherein the basic position is provided for the walking mode.

20. The wearable sitting posture assisting device according to claim 13, wherein the sitting means provides a virtual chair edge for the at least partly sitting posture.

* * * * *